(12) United States Patent
Sohn et al.

(10) Patent No.: US 6,417,383 B1
(45) Date of Patent: Jul. 9, 2002

(54) THERMOSENSITIVE CYCLOTRIPHOSPHAZENE DERIVATIVES AND A PREPARATION METHOD THEREOF

(75) Inventors: Youn Soo Sohn; Soo-Chang Song; Sang Beom Lee, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/869,761

(22) PCT Filed: Jan. 20, 2000

(86) PCT No.: PCT/KR00/00043

§ 371 (c)(1),
(2), (4) Date: Oct. 2, 2001

(87) PCT Pub. No.: WO01/30668

PCT Pub. Date: May 10, 2001

(30) Foreign Application Priority Data

Nov. 5, 1999 (KR) ............................................. 99-48800

(51) Int. Cl.$^7$ .................................................. C07F 9/02
(52) U.S. Cl. .............................. 558/87; 558/89; 558/90; 558/156; 558/157
(58) Field of Search .............................. 558/87, 89, 90, 558/156, 157

(56) References Cited

U.S. PATENT DOCUMENTS 3,985,834 A * 10/1976 Kao ........................... 260/927
5,104,947 A * 4/1992 Schacht et al. ............. 525/538
6,333,422 B1 * 12/2001 Sohn et al. .................. 556/17

* cited by examiner

Primary Examiner—Floyd D. Higel
Assistant Examiner—Golam M. M. Shameem
(74) Attorney, Agent, or Firm—Morrison & Foerster LLP

(57) ABSTRACT

The present invention relates to novel cyclotriphosphazene derivatives represented by Formula (1) and a preparation method thereof wherein HNA is an amino acid group selected from glycine group($-NHCH_2COO^-$), aminomalonic acid group($-NHCH(COO^-)_2$), aspartic acid group ($-NHCH(CH_2COO^-)COO^-$) and glutamic acid group ($-NHCH(CH_2CH_2COO^-)COO^-$), m is a repeating unit of poly(alkoxyethyleneglycol) selected from 2, 7, 12 and 16, and n is an integer representing number of alkyl carbons and selected from 0, 1, and 3.

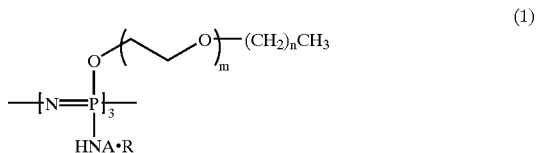

(1)

10 Claims, No Drawings

THERMOSENSITIVE CYCLOTRIPHOSPHAZENE DERIVATIVES AND A PREPARATION METHOD THEREOF

This application is a 371 of PCT/KR00/00043 Jan. 20, 2000.

BACKGROUND OF THE INVENTION

The present invention relates to a temperature-sensitive cyclotriphosphazene derivatives and a preparation method thereof. More particularly, the present invention relates to cyclotriphosphazene derivatives represented by Formula 1 that have thermosensitivity and a stereo-specific chemical structure, and preparation method thereof.

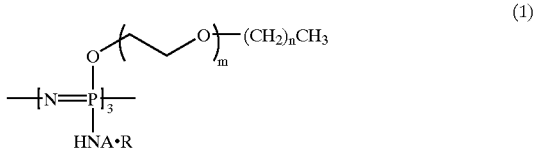

(1)

(wherein HNA is an amino acid group selected from glycine ($-NHCH_2COO^-$), aminomalonic acid ($-NHCH(COO^-)_2$), aspartic acid ($-NHCH(CH_2COO^-)COO^-$) and glutamic acid ($-NHCH(CH_2CH_2COO^-)COO^-$), R is either ethyl or benzyl, m is a repeating unit of poly(alkoxyethyleneglycol) selected from 2, 7, 12 and 16, and n is an integer representing the number of alkyl carbons selected from 0, 1, and 3).

The present inventors have found that the cyclotriphosphazene compounds, obtained by substituting the chlorine atoms in hexachlorocyclotriphosphazene ($N_3P_3Cl_6$) with a low- or high-molecular weight poly(alkoxyethyleneglycol) and amino acid ester, show a diverse thermosensitivity in an aqueous environment depending on their chemical structures.

Thermosensitivity in the present invention refers to the reversible phenomenon wherein a material is dissolved in water at a low temperature but precipitated as a result of the lowered solubility above at a critical temperature, and re-dissolved in water by lowering the temperature. This phenomenon is contradictory to the general phenomenon that solubility increases at higher temperatures. Thermosensitivity is often observed for water-soluble polymers that are dissolved below and precipitated above the so-called lower critical solution temperatures (LCST). Below the LCST, interaction between polymer and water molecules by hydrogen bonding is greater than the intermolecular hydrophobic interaction between polymer molecules, which results in dissolution of the polymer in water. As the temperature of the aqueous solution increases, however, the hydrogen bonding of the polymer-water molecules weakens whereas the hydrophobic interaction between the polymer molecules increases. As, the temperature of the aqueous solution reaches the LCST, the hydrophobic interaction becomes greater than the hydrogen bonding interaction between the polymer and water molecules resulting in the precipitation of the polymer in aqueous solution.

Thermosensitivity is found mainly among the hydrophilic polymers and non-ionic surfactant oligomers. The hydrophilic polymers exhibiting thermosensitivity are categorized as poly(ethyleneglycol) and organic polymers is wherein the hydrophobic and hydrophilic groups are bound together. The LCST of the hydrophilic poly(ethyleneglycol) depends on the molecular weight. Below the molecular weight of 200,000, the LCST is not observed (Bailey, F. E. et. al., *Poly(ethyleneoxide)*, Academic Press, New York, 1976). Above the molecular weight of 200,000, the LCST decreases as the molecular weight of the polymer increases. The LCST of the hydrophilic organic polymers changes depending on the ratio between the hydrophobic and hydrophilic groups. Generally, as the content of the hydrophilic group increases, the phase transition temperature increases. On the other hand, as the content of the hydrophobic group increases, the phase transition temperature decreases. The thermosensitivity of the non-ionic surfactant follows the same rule as the hydrophilic organic polymers.

These temperature-sensitive polymers and surfactants are widely applied in many fields, including drug delivery systems, medical biomaterials, thin films, separation of biochemical reactions, cosmetics and optics. One of the important features of the temperature-sensitive materials is that an organic solvent is not needed to load the drugs. Most of the biologically active materials lose their activity when exposed to organic solvents or high temperatures. By using the temperature-sensitive materials, however, drugs can be loaded at a lower temperature in an aqueous environment. Subsequently, the temperature can be increased to above the LCST to induce precipitation for drug loading. The most widely studied drug delivery systems using thermosensitive polymer is poly(N-isopropyl acrylamide) whose LCST is 33.2° C. Examples include studies on heparin, an anticoagulant, release from thermosensitive polymer coatings (Gutowska, A. et. al., *J. Biomedical materials Research*, 29, 811(1995)) and on catalytic activity changes across the LCST of the enzymes loaded in a thermosensitive gel (Chang, L. et. al., *J. Controlled Release*, 4, 223(1986)). In a study regarding membrane permeability of a drug using temperature-sensitive polymers was observed the membrane permeability of insulin through temperature-sensitive polymers (Bae, Y. H. et. al., *J. Controlled Release*, 9, 271(1989)). There are other reports on the poly(ethyleneglycol) co-polymer, hydroxy polymers and inorganic polyphosphazenes (Tanigami, T. et. al., *Macromolecules*, 22, 1397 (1989), Allock, H. R. et. al., *Macromolecules*, 25, 5573 (1992), Allock, H. R. et. al., *Macromolecules*, 29, 1313 (1996)).

Most of these existing techniques are related to non-degradable polymers, and thus have limitations in practical application to drug delivery systems. This is because non-degradable polymers can be toxic since they may be accumulated or generate toxic side-products in, human body. Also the high molecular weight of these polymers makes them bio-incompatible, and limits their application to drug delivery systems. Especially, these existing thermosensitive polymers could not be designed to have a desirable LCST for a particular purpose, since the ratio between the hydrophilic and hydrophobic moieties can not be modified easily. Therefore, there has been a need to develop an oligomeric drug delivery system which is biodegradable and whose thermosensitivity can be controlled accurately. Recently, the present inventors have discovered polyphosphazenes that have thermosensitivity (Song, S.-C. et. al., Macromolecules, 32, 2188 (1999)) and bio-degradability (Lee, S.B. et. al., Macromolecules, in press (1999)) simultaneously. Up to date, the temperature-sensitive oligomeric materials have been the non-ionic surfactant. This non-ionic surfactant, however, can not be applied to a drug delivery system, since they contain non-degradable hydrophobic alkyl chains. Moreover, thermosensitive oligomeric cyclotriphosphazenes are yet to be reported. In the present invention, thermosensitive oligomeric cyclotriphosphazenes have been developed for the first time whose LCST can be accurately controlled.

SUMMARY OF THE INVENTION

Therefore, an object of the present invention is to provide novel oligomeric cyclotriphosphazenes whose thermosensitivity can be accurately controlled.

Another object of the present invention is to provide a method of preparing the thermosensitive oligomeric cyclotriphosphazenes by substitution of the chloride atoms of hexachlorocyclotriphosphazene with a poly(alkoxyethyleneglycol) and an amino acid ester to have a stereo-specific chemical structure and to control their LCST accurately.

To achieve the above-mentioned objects, the present inventors have found that various temperature-sensitive cyclotriphosphazenes can be synthesized by reacting a hexachlorocyclotriphosphazene with hydrophilic poly(alkoxyethyleneglycols) having different molecular weights and successively with a variety of hydrophobic amino acid esters. Especially, it has been found that the LCST of the resultant cyclotriphosphazene derivatives can be controlled according to the desired purposes, since the LCST of the cyclotriphosphazene depends on the composition of poly(alkoxyethyleneglycol) and amino acid ester and on the lengths of the poly(alkoxyethyleneglycol) and terminal hydrophobic alkyl chains.

DETAILED DESCRIPTION OF THE INVENTION

The preparation method of cyclotriphosphazene derivatives represented by Formula 1 and which have stereo-specific chemical structure are explained in more detail as follows. The final product of Formula 1 is very stable against moisture in the air, but most of the intermediates are very sensitive to moisture. Therefore, all the procedures were performed under a vacuum or nitrogen atmosphere, and the solvents, tetrahydrofuran, benzene and toluene were thoroughly dried before use.

Poly(alkoxyethyleneglycol) of Formula 2 and benzene were azeotropically distilled at 70~80° C. to remove excess water and then dried completely for 3 days under vacuum at 80~90° C. in an oil bath before reaction.

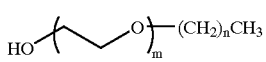
(2)

(wherein m and n are identical to those defined in Formula 1)

The dried alcohol of Formula 2 was reacted with an alkali metal such as sodium or potassium to produce an alkoxide metal salt of Formula 3, which was then reacted with hexachlorocyclotriphosphazene of Formula 4.

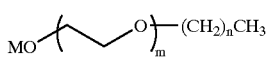
(3)

(wherein M is sodium or potassium, and m and n are identical to those defined in Formula 1)

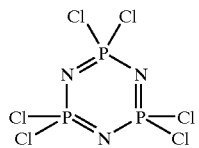
(4)

The above reaction are explained in more detail as follows. First, alcohol of Formula 2 is reacted with 1.5 equivalent weight of sodium or potassium in tetrahydrofuran (THF), benzene or toluene to prepare an metal alkoxide form of Formula 3. A non-geminal and cis-isomeric cyclotriphosphazene intermediate of Formula 5 is prepared by adding dropwise 3–4 equivalent weight of the alkoxide of Formula 3 to a solution containing 1 mole (6 equivalent weight) of hexachlorocyclotriphosphazene of Formula 4 and 2 equivalent weight of triethylamine and by reacting the mixture solution in a dry ice-acetone bath for 24 hours and further at room temperature for 10–12 hours.

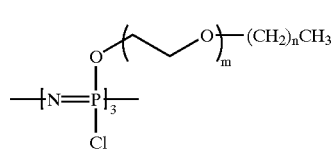
(5)

(wherein m and n are identical to those defined in Formula 1)

To the above solution, a solution containing 2 equivalent weight of amino acid ester of Formula 6 per remaining chlorine atoms in cyclotriphosphazene intermediate of Formula 5 and 4 equivalent weight of triethylamine per amino acid ester of Formula 6 was added dropwise, and the solution mixture was reacted for 2–4 hours at room temperature and continuously for 1–3 days at 40~60° C.

$$R.ANH.HCl \qquad (6)$$

(wherein m and n are identical to those defined in Formula 1)

The reaction mixture was centrifuged or filtered to remove precipitates ($Et_3N.HCl$ or NaCl). The filtrate was concentrated at a reduced pressure until only a small amount of the solvent remained. To the filtrate, excess amount of ether or hexane was added to induce precipitation. The precipitate was dissolved in a minimum amount of acetone and then excess hexane was added to precipitate the product. After repeating this procedure 2–3 times, the precipitate was purified by dissolving it in ethyl acetate and extracting with water, or by dissolving it in water and then dialyzing by using a membrane (molecular weight cutoff<1000). This purified solution was evaporated to dryness under reduced pressure. To remove other trace isomers, the product was dissolved in distilled water, and the agent to lower the LCST (NaCl, KCl, $CF_3CH_2OH$, or $CH_3(CH_2)_3OH$ was added to the mixture to induce precipitation. After centrifuging the mixture, the supernatant water was decanted. After repeating the above procedure 2–3 times, the product was vacuum-dried to obtain the final triphosphazene product of Formula 1.

The preparation procedure of the present invention is represented in the following Reaction Scheme 1.

Reaction Scheme 1

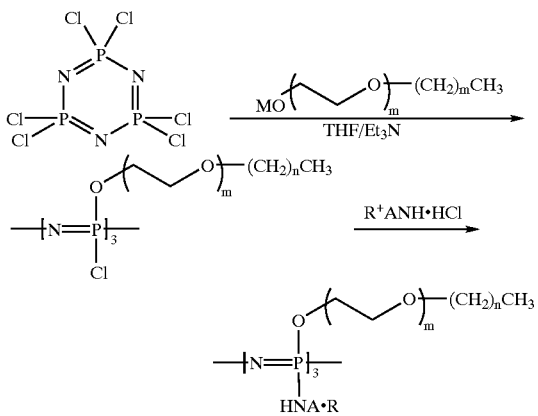

The present invention will be further illustrated by the following examples. It will be apparent to those having conventional knowledge in the field that these examples are given only to explain the present invention more clearly; but the invention is not limited to the examples given.

Elemental analysis of carbon, hydrogen, nitrogen in the compounds of the present invention was performed in the Special Analysis Center in our Institute by using a carbon, hydrogen and nitrogen analyzer (Perkin Eimer), and phosphorous analysis was performed using a Polyscan 61E ICP. Also, hydrogen and phosphorous nuclear magnetic resonance spectra were obtained using a Varian Gemini-300, and the LCST was measured by using a Perkin-Elmer Lamda18 UV/VIS spectrophotometer.

EXAMPLE 1

Preparation of (2-(2'-Methoxyethoxy)ethoxy) (glycineethylester)cyclotriphosphazene, $N_3P_3$ $((OCH_2CH_2)_2OCH_3)_3(NHCH_2COOC_2H_5)_3$ Sodium salt of 2-(2'-methoxyethoxy)ethoxide was prepared by refluxing 2-(2'-methoxyethoxy)ethanol (2.41 g, 20.1 mmol) and sodium metal (0.69 g, 30.2 mmol) in dry tetrahydrofuran for 48 hours in a nitrogen atmosphere. Hexachlorocyclotriphosphazene (2.00 g, 5.75 mmol) and triethylamine (1.16 g, 11.5 mmol) were dissolved in the same solvent and cooled in a dry ice-acetone bath. The previously prepared 2-(2'-methoxyethoxy)ethoxide solution was added dropwise to this cooled solution. The dry ice-acetone bath was removed after 2 hours. After the reaction was continued for 12 hours at room temperature, triethylamine (10.2 g, 103 mmol) and glycinethylesterhydrochloride (4.82 g, 34.5 mmol) were added and reacted for 2 hours at room temperature and for another 48 hours at 50° C. The reaction mixture was filtered to remove the precipitates ($Et_3N.HCl$ or NaCl). The filtrate was concentrated at reduced pressure until only a small amount of the solvent remained. To the filtrate, excess amount of hexane was added to induce precipitation. After repeating 2–3 times the procedure of dissolving the obtained precipitates in a small amount of acetone and precipitating by adding hexane, the precipitate was dissolved in 25 ml of ethylacetate and extracted with distilled water 2–3 times to remove the remaining salts and the dried in a vacuum drier. To remove other trace isomers, the viscous liquid obtained above was dissolved in water (70 ml), and $CF_3CH_2OH$ (13 g), an agent to lower the LCST, was added to the mixture to induce precipitation. After centrifuging the mixture, the supernatant water was decanted. After repeating the above procedure 3 times, the product was vacuum-dried to obtain 3.43 g (yield, 74.7%) of the final triphosphazene product.

Molecular formula: $C_{27}H_{57}N_6O_{15}P_3$

Elemental analysis (%): C, 40.00; H, 7.21; N, 10.20; P, 11.60; Theoretical value: C, 40.60; H, 7.19; N, 10.52; P, 11.63; $^1$H-NMR spectrum ($D_2O$, ppm); δ 1.2–1.4 (b, 3H, —NHCH$_2$COOCH$_2$C$\underline{H}_3$), δ 3.4 (s, 3H, —O(CH$_2$CH$_2$O)$_2$C$\underline{H}$), δ 3.6–3.9 (b, 8H, —OCH$_2$C$\underline{H}_2$OC$\underline{H}_2$CH$_2$OCH$_3$, —NHC$\underline{H}_2$COOCH$_2$CH$_3$), δ 4.0–4.1 (b, 2H, —OC$\underline{H}_2$CH$_2$OCH$_2$CH$_2$OCH$_3$), δ 4.2–4.3 (b, 2H, —NHCH$_2$COOC$\underline{H}_2$CH$_3$); $^{31}$P-NMR spectrum (acetone-d$_6$, ppm); δ 43.75; Glass transition temperature ($T_g$): −56.42° C.; LCST: not observed (above 100° C.)

EXAMPLE 2

Preparation of (2-(2'-Methoxyethoxy)ethoxy) (glycinebenzylester) cyclotriphosphazene, $N_3P_3$ $((OCH_2CH_2)_2OCH_3)_3(NHCH_2COOCH_2C_6H_5)_3$ The procedure for Example 1 was followed by using 2-(2'-methoxyethoxy)ethanol (2.41 g, 20.1 mmol), sodium metal (0.69 g, 30.2 mmol), hexachlorocyclotriphosphazene (2.00 g, 5.75 mmol), triethylamine (10.1 g, 103 mmol) and glycinebenzylester-p-toluenesulfonic acid salt (11.6 g, 34.5 mmol) to obtain 2.12 g (yield, 74.9%) of the final triphosphazene product, $N_3P_3((OCH_2CH_2)_2OCH_3)_3$ $(NHCH_2COOCH_2C_6H_5)_3$.

Molecular formula: $C_{42}H_{53}N_6O_{15}P_3$

Elemental analysis (%): C, 50.70; H, 6.55; N, 8.28; P, 9.48; Theoretical value: C, 51.22; H, 6.56; N, 8.53; P, 9.43; $^1$H-NMR spectrum (CDCl$_3$, ppm); δ 3.4 (s, 3H, —O(CH$_2$C$\underline{H}_2$O)$_2$CH$_3$), δ 3.5–3.6 (s, 2H, —OCH$_2$C$\underline{H}_2$OCH$_2$C$\underline{H}_2$OCH$_3$), δ 3.6–3.8 (b, 6H, —OCH$_2$C$\underline{H}_2$OC$\underline{H}_2$CH$_2$OCH$_3$, —NHC$\underline{H}_2$COOCH$_2$C$_6$H$_5$), δ 4.0–4.1 (b, 2H, —OC$\underline{H}_2$CH$_2$OCH$_2$C$\underline{H}_2$OCH$_3$), δ 5.1–5.2 (s, 2H, —NHCH$_2$COOC$\underline{H}_2$C$_6$H$_5$), δ 7.3–7.4 (s, 5H, —NHCH$_2$COOCH$_2$C$_6$H$_5$); $^{31}$P-NMR spectrum (acetone-d$_6$, ppm); δ 43.73; Glass transition temperature ($T_g$): −44.99° C.; LCST: 10.5° C.

EXAMPLE 3

Preparation of (2-(2'-Methoxyethoxy)ethoxy)- (aminomalonatodiethylester) cyclotriphosphazene, $N_3P_3((OCH_2CH_2)_2OCH_3)_3(NHCH_2(COOC_2H_5)_2)_3$ The procedure for Example I was followed by using 2-(2'-methoxyethoxy)ethanol (2.41 g, 20.1 mmol), sodium metal (0.69 g, 30.2 mmol), hexachlorocyclotriphosphazene (2.00 g, 5.75 mmol), triethylamine (10.2 g, 103 mmol) and aminomalonatodiethylester hydrogen chloride salt (6.89 g, 34.5 mmol) to obtain 4.1 g (yield, 70.5%) of the final triphosphazene product, $N_3P_3((OCH_2CH_2)_2OCH_3)_3$ $(NHCH_2(COOC_2H_5)_2)_3$.

Molecular formula: $C_{36}H_{69}N_5O_{21}P_3$

Elemental analysis (%): C, 42.18; H, 6.91; N, 8.09; P, 9.20; Theoretical value: C, 42.61; H, 6.85; N, 8.28; P, 9.16; $^1$H-NMR spectrum ($D_2O$, ppm); δ 1.2–1.4 (b, 6H, —NHCH(COOCH$_2$C$\underline{H}_3$)$_2$), δ 3.4 (s, 3H, —O(CH$_2$CH$_2$O)$_2$C$\underline{H}_3$), δ 3.6–3.8 (b, 6H, —OCH$_2$C$\underline{H}_2$OC$\underline{H}_2$CH$_2$OCH$_3$), δ 4.0–4.1 (b, 2H, —OC$\underline{H}_2$CH$_2$OCH$_2$C$\underline{H}_2$OCH$_3$), δ 4.2–4.4 (b, 4H, —NHCH(COOC$\underline{H}_2$CH$_3$)$_2$), δ 4.6–4.7 (b, 1H, —NHC$\underline{H}$(COOCH$_2$CH$_3$)$_2$); $^{31}$P-NMR spectrum (acetone-d$_6$, ppm); δ 41.60; Glass transition temperature ($T_g$): −47.96° C.; LCST: 39.0° C.

EXAMPLE 4

Preparation of (2-(2'-Methoxyethoxy)ethoxy)(L-aspartoyldiethylester) cyclotriphosphazene, $N_3P_3$ $((OCH_2CH_2)_2OCH_3)_3(NHCH(CH_2COOC_2H_5)$ $COOC_2H_5)_3$ The procedure for Example 1 was followed by using 2-(2'-methoxyethoxy)ethanol (2.41 g, 20.1 mmol), sodium metal (0.69 g, 30.2 mmol), hexachlorocyclotriphosphazene (2.00 g, 5.75 mmol), triethylamine (10.2 g, 103 mmol) and L-aspartoyldiethylester hydrogen chloride salt (7.37 g, 34.5 mmol) to obtain 4.70 g (yield, 77.3%) of the final triphosphazene product, $N_3P_3((OCH_2CH_2)_2OCH_3)_3(NHCH(CH_2COOC_2H_5)COOC_2H_5)_3$.

Molecular formula: $C_{39}H_{75}N_6O_{21}P_3$

Elemental analysis (%): C, 43.30; H, 7.22; N, 7.83; P, 8.87; Theoretical value: C, 44.32; H, 7.15; N, 7.95; P, 8.79; $^1$H-NMR spectrum ($D_2O$, ppm): δ 1.2–1.4 (b, 6H, —NHCH($CH_2OOCH_2C\underline{H}_3$)($COOCH_2C\underline{H}_3$)), δ 2.9–3.1 (b, 2H, —NHCH($C\underline{H}_2OOCH_2CH_3$)($COOCH_2CH_3$)), δ 3.4 (s, 3H, —O($CH_2CH_2O)_2C\underline{H}_3$), δ 3.6–3.8 (b, 6H, —OCH$_2$C$\underline{H}^2$OC$\underline{H}_2$C$\underline{H}_2$OCH$_3$), δ 4.0–4.1 (b, 2H, —OC$\underline{H}_2$CH$_2$OCH$_2$CH$_2$OCH$_3$), δ 4.2–4.4 (b, 5H, —NHC$\underline{H}$(CH$_2$OOC$\underline{H}_2$CH$_3$)(COOC$\underline{H}_2$CH$_3$)); $^{31}$P-NMR spectrum (acetone-$d_6$, ppm): δ 42.23 Glass transition temperature ($T_g$): –29.43° C.; LCST: 47.5° C.

EXAMPLE 5

Preparation of (2-(2'-Methoxyethoxy)ethoxy)(L-glutamoyldiethylester) cyclotriphosphazene, $N_3P_3((OCH_2CH_2)_2OCH_3)_3(NHCH(CH_2CH_2COOC_2H_5)COOC_2H_5)_3$ The procedure for Example 1 was followed by using 2-(2'-methoxyethoxy)ethanol (2.41 g, 20.1 mmol), sodium metal (0.69 g, 30.2 mmol), hexachlorocyclotriphosphazene (2.00 g, 5.75 mmol), triethylamine (10.2 g, 103 mmol) and L-glutamoyldiethylester hydrogen chloride salt (8.27 g, 34.5 mmol) to obtain 1.07 g (yield, 17.2%) of the final triphosphazene product, $N_3P_3((OCH_2CH_2)_2OCH_3)_3(NHCH(CH_2CH_2CH_2H_5)COOC_2H_5)_3$.

Molecular formula: $C_{42}H_{81}N_6O_{21}P_3$

Elemental analysis (%): C, 45.31; H, 7.47; N, 7.71; P, 8.49. Theoretical value: C, 45.90; H, 7.42; N, 7.65; P. 8.45; $^1$H-NMR spectrum (CDCl$_3$, ppm): δ 1.2–1.4 (b, 6H, —NHCH($CH_2CH_2OOCH_2C\underline{H}_3$)($COOCH_2C\underline{H}_3$)), δ 2.0–2.2 (b, 2H, —NHCH($C\underline{H}_2CH_2OOCH_2CH_3$)($COOCH_2CH_3$)), δ 2.4–2.5 (b, 2H, —NHCH($CH_2C\underline{H}_2OOCH_2CH_3$)($COOCH_2CH_3$)), δ 3.4 (s, 3H, —O($CH_2CH_2O)_2C\underline{H}_3$), δ 3.6–3.8 (b, 6H, —OCH$_2$C$\underline{H}_2$OCH$_2$C$\underline{H}_2$OCH$_3$), δ 4.0–4.1 (b, 2H, —OC$\underline{H}_2$CH$_2$OCH$_2$CH$_2$OCH$_3$), δ 4.2–4.4 (b, 5H, —NHC$\underline{H}$(CH$_2$CH$_2$OOC$\underline{H}_2$CH$_3$)(COOC$\underline{H}_2$CH$_3$)); $^{31}$P-NMR spectrum (acetone-$d_6$, ppm): δ 42.46; Glass transition temperature ($T_g$): –51.99° C.; LCST: 30.0° C.

EXAMPLE 6

Preparation of (2-(2'-Ethoxyethoxy)ethoxy)(L-aspartoyldiethylester) cyclotriphosphazene, $N_3P_3((OCH_2CH_2)_2OC_2H_5)_3(NHCH(CH_2COOC_2H_5)COOC_2H_5)_3$ The procedure for Example 1 was followed by using 2-(2'-ethoxyethoxy)ethanol (2.70 g, 20.1 mmol), sodium metal (0.69 g, 30.2 mmol), hexachlorocyclotriphosphazene (2.00 g, 5.75 mmol), triethylamine (10.2 g, 103 mmol) and L-aspartoyldiethylester hydrogen chloride salt (7.37 g, 34.5 mmol) to obtain 8.01 g (yield, 63.4%) of the final triphosphazene product, $N_3P_3((OCH_2CH_2)_2OC_2H_5)_3(NHCH(CH_2COOC_2H_5)COOC_2H_5)_3$.

Molecular formula: $C_{42}H_{81}N_6O_{21}P_3$

Elemental analysis (%): C, 44.61; H. 7.64; N. 7.54; P, 8.59; Theoretical value: C, 45.90; H, 7.42; N, 7.65; P, 8.45; $^1$H-NMR spectrum (CDCl$_3$, ppm): δ 1.1–1.4 (b, 9H, —NHCH($CH_2OOCH_2C\underline{H}_3$)($COOCH_2C\underline{H}_3$), —OCH$_2$CH$_2$OCH$_2$CH$_2$OCH$_2$C$\underline{H}_3$), δ 2.8–3.0 (b, 2H, —NHCH($C\underline{H}_2OOCH_2CH_3$)($COOCH_2CH_3$)), δ 3.5–3.8 (b, 8H, —OCH$_2$C$\underline{H}_2$OCH$_2$C$\underline{H}_2$OCH$_2$CH$_3$), δ 4.0–4.1 (b, 2H, —OC$\underline{H}_2$CH$_2$OC$\underline{H}_2$CH$_2$OCH$_2$CH$_3$), δ 4.2–4.4 (b, 5H, —NHC$\underline{H}$(CH$_2$OOC$\underline{H}_2$CH$_3$)(COOC$\underline{H}_2$CH$_3$)); $^{31}$P-NMR spectrum (acetone-$d_6$, ppm): δ 42.26; Glass transition temperature ($T_g$): –39.66° C.; LCST: 16.5° C.

EXAMPLE 7

Preparation of (2-(2'-Butoxyethoxy)ethoxy)(L-aspartoyldiethylester) cyclotriphosphazene, $N_3P_3((OCH_2CH_2)_2OC_4H_9)_3(NHCH(CH_2COOC_2H_5)COOC_2H_5)_3$ The procedure for Example 1 was followed by using 2-(2'-butoxyethoxy)ethanol (3.27 g, 20.1 mmol), sodium metal (0.69 g, 30.2 mmol), hexachlorocyclotriphosphazene (2.00 g, 5.75 mmol), triethylamine (10.2 g, 103 mmol), and L-aspartoyldiethylester hydrogen chloride salt (7.37 g, 34.5 mmol) to obtain 4.75 g (yield, 69.8%) of the final triphosphazene product, $N_3P_3((OCH_2CH_2)_2OC_4H_9)_3(NHCH(CH_2COOC_2H_5)COOC_2H_5)_3$.

Molecular formula: $C_{48}H_{93}N_6O_{21}P_3$

Elemental analysis (%): C, 48.09; H, 7.88, N, 7.19; P, 7.81; Theoretical value: C, 48.73; H, 7.92; N, 7.10; P, 7.85; $^1$H-NMR spectrum (CDCl$_3$, ppm): δ 0.8–1.0 (b, 3H, —OCH$_2$CH$_2$OCH$_2$CH$_2$OCH$_2$CH$_2$CH$_2$C$\underline{H}_3$), δ 1.2–1.4 (b, 8H, —NHCH($CH_2OOCH_2C\underline{H}_3$)($COOCH_2C\underline{H}_3$), —OCH$_2$CH$_2$OCH$_2$CH$_2$OCH$_2$C$\underline{H}_2$CH$_3$), δ 1.5–1.6 (b, 2H, —OCH$_2$CH$_2$OCH$_2$CH$_2$OC$\underline{H}_2$OCH$_2$CH$_3$), δ 2.8–3.0 (b, 2H, —NHCH($C\underline{H}_2OOCH_2CH_3$)($COOCH_2CH_3$)), δ 3.4 (s, 2H, —OCH$_2$CH$_2$OCH$_2$CH$_2$OC$\underline{H}_2$CH$_2$CH$_2$CH$_3$), δ 3.5–3.8 (b, 6H, —OCH$_2$C$\underline{H}_2$OCH$_2$C$\underline{H}_2$OCH$_2$CH$_2$CH$_3$), δ 4.0–4.1 (b, 2H, —OC$\underline{H}_2$CH$_2$OC$\underline{H}_2$CH$_2$OCH$_2$C$\underline{H}_2$CH$_3$), δ 4.2–4.4 (b, 5H, —NHC$\underline{H}$(CH$_2$OOC$\underline{H}_2$CH$_3$)(COOC$\underline{H}_2$CH$_3$)); $^{31}$P-NMR spectrum (acetone-$d_6$, ppm): δ 42.22; Glass transition temperature ($T_g$): –34.86° C.; LCST: not observed (below 0° C.)

EXAMPLE 8

Preparation of (Poly(methoxyethyleneglycol350))(glycinebenzylester) cyclotriphosphazene, $N_3P_3(OCH_2CH_2)_7OCH_3)_3(NHCH_2COOCH_2C_6H_5)_3$ The procedure for Example 1 was followed by using poly(methoxyethyleneglycol) of molecular weight 350 (7.05 g, 20.1 mmol), sodium metal (0.69 g, 30.2 mmol), hexachlorocyclotriphosphazene (2.00 g, 5.75 mmol), triethylamine (10.2 g, 103 mmol) and glycinebenzylester-p-toluenesulfonic acid salt (11.6 g, 34.5 mmol) to obtain 8.32 g (yield, 87.9%) of the final triphosphazene product, $N_3P_3(OCH_2CH_2)_7OCH_3)_3(NHCH_2COOCH_2C_6H_5)_3$.

Molecular formula: $C_{72}H_{123}N_6O_{30}P_3$

Elemental analysis (%): C, 51.40; H. 7.62; N, 5.02; P, 5.61; Theoretical value: C, 52.55; H, 7.53; N, 5.11; P, 5.65; $^1$H-NMR spectrum ($D_2O$, ppm): δ 3.4 (s, 3H, —OCH$_2$CH$_2$O(CH$_2$CH$_2$O)$_6$C$\underline{H}_3$), δ 3.6–3.8 (s, 28H, —OCH$_2$C$\underline{H}_2$O(C$\underline{H}_2$C$\underline{H}_2$O)$_6$CH$_3$, —NHC$\underline{H}_2$COOCH$_2$C$_6$H$_5$), δ 4.0–4.1 (b, 2H, —OC$\underline{H2}$CH$_2$O(CH$_2$CH$_2$O)$_6$CH$_3$), δ 5.1–5.2 (b, 2H, —NHCH$_2$COOC$\underline{H}_2$C$_6$H$_5$), δ 7.3–7.4 (b, 5H, —NHCH$_2$COOCH$_2$C$_6$$\underline{H}_5$); $^{31}$P-NMR spectrum (acetone-$d_6$, ppm): δ 43.74; Glass transition temperature ($T_g$): –52.78° C.; LCST: 65.5° C.

EXAMPLE 9

Preparation of (Poly(methoxyethyleneglycol350))(aminomalonatoyl diethylester)cyclotriphosphazene, $N_3P_3(OCH_2CH_2)_7OCH_3)_3(NHCH(COOC_2H_5)_2)_3$ The procedure for Example 1 was followed by using poly(methoxyethyleneglycol) of molecular weight 350 (7.05 g, 20.1 mmol), sodium metal (0.69 g, 30.2 mmol), hexachlorocyclotriphosphazene (2.00 g, 5.75 mmol), triethylamine (10.2 g, 103 mmol) and aminomalonatodiethylester hydrogen chloride salt (7.30 g, 34.5 mmol) to obtain 8.20 g (yield, 85.2%) of the final triphosphazene product, $N_3P_3(OCH_2CH_2)_7OCH_3)_3(NHCH_2COOCH_2C_6H_5)_3$.

Molecular formula: $C_{66}H_{129}N_6O_{36}P_3$

Elemental analysis (%): C, 46.10; H, 7.82; N, 4.91 P, 5.60; Theoretical value: C, 47.31; H, 7.76; N, 5.02; P, 5.55; $^1$H-NMR spectrum ($D_2O$, ppm): δ 1.3–1.4 (b, 6H, —NHCH (COOCH$_2$C$\underline{H}_3$)$_2$), δ 3.4 (s, 3H, —OCH$_2$CH$_2$O(CH$_2$ CH$_2$O)$_6$ C$\underline{H}_3$), δ 3.6–3.8 (b, 26H, —OCH$_2$C$\underline{H}_2$O(C$\underline{H}_2$C$\underline{H}_2$O)$_6$CH$_3$), δ 4.1–4.2 (b, 2H, —OC$\underline{H}_2$CH$_2$O(CH$_2$CH$_2$O)$_6$CH$_3$), δ 4.3–4.4 (b, 4H, —NHCH(COOC$\underline{H}_2$CH$_3$)$_2$), δ 4.7–4.8 (b, 1 H, —NHC$\underline{H}$(COOCH$_2$CH$_3$)$_2$); $^{31}$P-NMR spectrum (acetone-d$_6$, ppm): δ 41.63; Glass transition temperature ($T_g$): −60.97° C.; LCST: 95.0° C.

EXAMPLE 10

Preparation of (Poly(methoxyethyleneglycol350)) (L-aspartoyldiethylester) cyclotriphosphazene, $N_3P_3(OCH_2CH_2)_7OCH_3)_3(NHCH(CH_2COOCH_3)COOCH_3)_3$ The procedure for Example 1 was followed by using poly(methoxyethyleneglycol) of molecular weight 350 (7.05 g, 20.1 mmol), sodium metal (0.69 g, 30.2 mmol), hexachlorocyclotriphosphazene (2.00 g, 5.75 mmol), triethylamine (10.2 g, 103 mmol) and L-aspartoyldiethylester hydrogen chloride salt (7.37 g, 34.5 mmol) to obtain 8.30 g (yield, 84.0%) of the final triphosphazene product, $N_3P_3(OCH_2CH_2)_7OCH_3)_3(NHCH(CH_2COOCH_3)COOCH_3)_3$.

Molecular formula: $C_{69}H_{135}N_6O_{36}P_3$

Elemental analysis (%): C, 47.70; H. 7.83; N, 4.95; P, 5.44; Theoretical value: C, 48.25; H, 7.92; N, 4.89; P. 5.41; $^1$H-NMR spectrum ($D_2O$, ppm): δ 1.2–1.4 (b, 6H, —NHCH (CH$_2$OOCH$_2$C$\underline{H}_3$)(COOCH$_2$C$\underline{H}_3$)), δ 2.9–3.1 (b, 2H, —NHCH(C$\underline{H}_2$OOCH$_2$CH$_3$)(COOCH$_2$CH$_3$)), δ 3.4 (s, 3H, —OCH$_2$CH$_2$O(CH$_2$CH$_2$O)$_6$C$\underline{H}_3$), δ 3.6–3.8 (b, 26H, —OCH$_2$C$\underline{H}_2$O(C$\underline{H}_2$C$\underline{H}_2$)$_6$CH$_3$), δ 4.0–4.1 (b, 2H, —OC$\underline{H}_2$ CH$_2$O (C$\underline{H}_2$CH$_2$O)$_6$CH$_3$), δ 4.2–4.4 (b, 5H. —NHC $\underline{H}$(CH$_2$OOC$\underline{H}_3$)(COOC$\underline{H}_2$CH$_3$)); $^{31}$P-NMR spectrum (acetone-d$_6$, ppm): δ 42.23; Glass transition temperature ($T_g$): −55.05° C.; LCST: 83.0° C.

EXAMPLE 11

Preparation of (Poly(methoxyethyleneglycol350)) (L-aspartoyldibenzylester)cyclotriphosphazene, $N_3P_3(OCH_2CH_2)_7OCH_3)_3(NHCH(CH_2COOCH_2C_6H_5)COOCH_2C_6H_5)_3$ The procedure for Example 1 was followed by using poly(methoxyethyleneglycol) of molecular weight 350 (7.05 g, 20.1 mmol), sodium metal (0.69 g, 30.2 mmol), hexachlorocyclotriphosphazene (2.00 g, 5.75 mmol), triethylamine (10.2 g, 103 mmol) and L-aspartoyldibenzylester-p-toluene sulfonic acid salt (16.7 g, 34.5 mmol) to obtain 10.2 g (yield, 84.8%) of the final triphosphazene product, $N_3P_3(OCH_2CH_2)_7OCH_3)_3(NHCH(CH_2COOCH_2C_6H_5)COOCH_2C_6H_5)_3$.

Molecular formula: $C_{99}H_{147}N_6O_{36}P_3$

Elemental analysis (%): C, 55.00; H, 7.20; N, 4.12; P, 4.39; Theoretical value: C, 56.89; H, 7.09; N, 4.02; P, 4.45; $^1$H-NMR spectrum ($D_2O$, ppm): δ 2.8–2.9 (b, 2H, —NHCH(C$\underline{H}_2$OOCH$_2$C$_6$H$_5$)(COOCH$_2$C$_6$H$_5$)), δ 3.4–3.5 (b, 3H, —OCH$_2$CH$_2$O(CH$_2$CH$_2$O)$_6$C$\underline{H}_3$), δ 3.6–3.8 (b, 26H, —OCH$_2$C$\underline{H}_2$O(C$\underline{H}_2$C$\underline{H}_2$O)$_6$CH$_3$), δ 4.0–4.1 (b, 2H, —OC$\underline{H}_2$CH$_2$O(C$\underline{H}_2$C$\underline{H}_2$O)$_6$CH$_3$), δ 4.2–4.4(b, 1H, —NHC $\underline{H}$(CH$_2$OOCH$_2$O$_6$H$_5$)(COOCH$_2$C$_6$H$_5$)), δ 5.0–5.2 (b, 4H, —NHCH(CH$_2$OOC$\underline{H}_2$C$_6$H$_5$)(COOC$\underline{H}_2$C$_6$H$_5$)), δ 7.0–7.3 (b, 10H, —NHCH(CH$_2$OOCH$_2$C$_6$$\underline{H}_5$)(COOCH$_2$C$_6$$\underline{H}_5$)); $^{31}$P-NMR spectrum (acetone-d$_6$, ppm): δ 42.21; Glass transition temperature ($T_g$): −44.91° C.; LCST: 42.5° C.

EXAMPLE 12

Preparation of (Poly(methoxyethyleneglycol350)) (L-glutamoyldiethylester) cyclotriphosphazene, $N_3P_3(OCH_2CH_2)_7OCH_3)_3(NHCH(CH_2CH_2COOC_2H_5)COOC_2H_5)_3$ The procedure for Example 1 was followed by using poly(methoxyethyleneglycol) of molecular weight 350 (7.05 g, 20.1 mmol), sodium metal (0.69 g, 30.2 mmol), hexachlorocyclotriphosphazene (2.00 g, 5.75 mmol), triethylamine (10.2 g, 103 mmol) and L-glutamoyldiethylester hydrogen chloride salt (7.86 g, 34.5 mmol) to obtain 8.78 g (yield, 86.8%) of the final triphosphazene product, $N_3P_3(OCH_2CH_2)_7OCH_3)_3(NHCH(CH_2CH_2COOC_2H_5)COOC_2H_5)_3$.

Molecular formula: $C_{72}H_{141}N_6O_{36}P_3$

Elemental analysis (%): C, 47.83; H, 7.98; N, 4.83; P, 5.22; Theoretical value: C, 49.14; H. 8.08; N, 4.78; P, 5.28; $^1$H-NMR spectrum ($D_2O$, ppm): δ 1.2–1.4 (b, 6H, —NHCH (CH$_2$CH$_2$OOCH$_2$C$\underline{H}_3$)(COOCH$_2$C$\underline{H}_3$)), δ 2.0–2.2 (b, 2H, —NHCH(C$\underline{H}_2$CH$_2$OOCH$_2$CH$_3$)(COOCH$_2$CH$_3$)), δ 2.4–2.5 (b, 2H, —NHCH(CH$_2$C$\underline{H}_2$OOCH$_2$CH$_3$)(COOCH$_2$CH$_3$)), δ 3.4 (s, 3H, —OCH$_2$CH$_2$O(CH$_2$CH$_2$O)$_6$C$\underline{H}_3$), δ 3.6–3.8 (b, 26H, —OCH$_2$C$\underline{H}_2$O(C$\underline{H}_2$C$\underline{H}_2$O)$_6$CH$_3$), δ 4.0–4.1 (b, 2H, —OC$\underline{H}_2$CH$_2$O(C$\underline{H}_2$CH$_2$O)$_6$CH$_3$), δ 4.2–4.4 (b, 5H, —NHC $\underline{H}$(CH$_2$CH$_2$OOC$\underline{H}_2$CH$_3$)(COOC$\underline{H}_2$CH$_3$)); $^{31}$P-NMR spectrum (acetone-d$_6$, ppm): δ 42.17; Glass transition temperature ($T_g$): −47.36° C.; LCST: 73.0° C.

EXAMPLE 13

Preparation of (Poly(methoxyethyleneglycols550)) L-aspartoyldibenzylester) cyclotriphosphazene, $N_3P_3(OCH_2CH_2)_{12}OCH_3)_3(NHCH(CH_2COOCH_2C_6H_5)COOCH_2C_6H_5)_3$ The procedure for Example 1 was followed by using poly(methoxyethyleneglycol) of molecular weight 550 (11.0 g, 20.1 mmol), sodium metal (0.69 g, 30.2 mmol), hexachlorocyclotriphosphazene (2.00 g, 5.75 mmol), triethylamine (10.2 g, 103 mmol) and L-aspartoyldibenzylester-p-toluene sulfonic acid salt (16.7 g, 34.5 mmol) to obtain 13.6 g (yield, 86.0%) of the final triphosphazene product, $N_3P_3(OCH_2CH_2)_{12}OCH_3)_3(NHCH(CH_2COOCH_2C_6H_5)COOCH_2C_6H_5)_3$.

Molecular formula: $C_{129}H_{207}N_6O_{51}P_3$

Elemental analysis (%): C, 57.07; H, 7.66; N, 3.12; P, 3.32; Theoretical value: C, 56.32; H, 7.58; N. 3.05; P, 3.38; $^1$H-NMR spectrum ($D_2O$, ppm) δ 2.8–2.9 (b, 2H, —NHCH(C$\underline{H}_2$OOCH$_2$C$_6$H$_5$)(COOCH$_2$C$_6$H$_5$)), δ 3.4–3.5 (b, 3H, —OCH$_2$CH$_2$O(CH$_2$CH$_2$O)$_{11}$C$\underline{H}_3$), δ 3.6–3.8 (b, 46H, —OCH$_2$C$\underline{H}_2$O(C$\underline{H}_2$C$\underline{H}_2$O)$_{11}$CH$_3$), δ 4.0–4.1 (b, 2H, —OC$\underline{H}_2$CH$_2$O(CH$_2$CH$_2$O)$_{11}$CH$_3$), δ 4.2–4.4 (b, 1H, —NHC$\underline{H}$(CH$_2$OOCH$_2$C$_6$H$_5$)(COOCH$_2$C$_6$H$_5$)), δ 5.0–5.2 (b, 4H, —NHCH(CH$_2$OOC$\underline{H}_2$C$_6$H$_5$)(COOC$\underline{H}_2$C$_6$H$_5$)), f 7.0–7.3 (b, 10H, —NHCH(CH$_2$OOCH$_2$C$_6$$\underline{H}_5$)(COOCH$_2$C$_6$ $\underline{H}$)); $^{31}$P-NMR spectrum (acetone-d$_6$, ppm): δ 41.97; Glass transition temperature ($T_g$): 45.28° C.; LCST: 69.0° C.

EXAMPLE 14

Preparation of (Poly(methoxyethyleneglycol750)) (L-aspartoyldibenzylester) cyclotriphosphazene, $N_3P_3(OCH_2CH_2)_{16}OCH_3)_3(NHCH(CH_2COOCH_2C_6H_5)COOCH_2C_6H_5)_3$ The procedure for Example 1 was followed by using poly(methoxyethyleneglycol) of molecular weight 3750

(15.1 g, 20.1 mmol), sodium metal (0.69 g, 30.2 mmol), hexachlorocyclotriphosphazene (2.00 g, 5.75 mmol), triethylamine (10.2 g, 103 mmol) and L-aspartoyldibenzylester-p-toluene sulfonic acid salt (16.7 g, 34.5 mmol) to obtain 15.5 g (yield, 82.3%) of the final triphosphazene product, $N_3P_3(OCH_2CH_2)_{16}$ $OCH_3)_3$ $(NHCH(CH_2COOCH_2C_6H_5)COOCH_2C_6H_5)_3$.

Molecular formula: $C_{153}H_{255}N_6O_{63}P_3$

Elemental analysis (%): C, 54.21; H, 7.77; N, 2.65; P, 2.86; Theoretical value: C, 56.03; H, 7.84; N, 2.56; P, 2.83; $^1$H-NMR spectrum ($D_2O$, ppm): δ 2.8–2.9 (b, 2H, —NHCH(C$\underline{H}_2$OOCH$_2C_6H_5$)(COOCH$_2C_6H_5$)), δ 3.4–3.5 (b, 3H, —OCH$_2$CH$_2$O(CH$_2$CH$_2$O)$_{15}$C$\underline{H}_3$), δ 3.6–3.8 (b, 62H, —OCH$_2$C$\underline{H}_2$O(C$\underline{H}_2$H)$_{15}$CH$_3$), δ 4.0–4.1 (b, 2H, —OC $\underline{H}_2$CH$_2$O(CH$_2$CH$_2$O)$_{15}$CH$_3$), δ 4.2–4.4 (b, 1H, —NHC $\underline{H}$(CH$_2$OOCH$_2C_6H_5$)(COOCH$_2C_6H_5$)), δ 5.0–5.2 (b, 4H, —NHCH(CH$_2$OOCC$\underline{H}_2C_6H_5$)(COOC$\underline{H}_2C_6H_5$)); δ 7.0–7.3 (b, 10H, —NHCH(CH$_2$OOCH$_2$C$\underline{H}_5$)(COOCH$_2C_6\underline{H}_5$)); $^{31}$P-NMR spectrum (acetone-$d_6$, ppm): δ 41.91; Glass transition temperature ($T_g$): −32.64° C.; LCST: 78.5° C.

According to the present invention, cyclotriphosphazenes having a stereo-specific chemical structure and thermosensitivity are provided. Thermosensitivity of cyclotriphosphazenes of the present invention can be designed for desired purposes. Therefore, the cyclotriphosphazenes of the present invention have a great potential for applications in many fields such as materials for drug delivery systems.

We claim:

1. A cyclotriphosphazene represented by Formula 1:

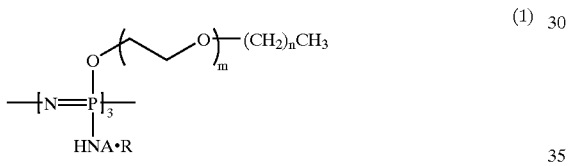
(1)

wherein HNA represents an amino acid group selected from the group consisting of —NHCH$_2$COO$^-$, —NHCH(COO$^-$)$_2$, —NHCH(CH$_2$COO$^-$)COO$^-$ and —NHCH(CH$_2$CH$_2$COO$^-$)COO$^-$, R represents either an ethyl or benzyl, m is an integer selected from the group consisting of 2, 7, 12 and 16, and n is an integer selected from the group consisting of 0, 1, and 3.

2. A preparation method of cyclotriphosphazene of Formula 1

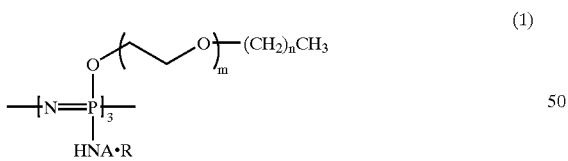
(1)

wherein HNA represents an amino acid group selected from the group consisting of —NHCH$_2$COO$^-$, —NHCH(COO$^-$)$_2$, —NHCH(CH$_2$COO$^-$)COO$^-$ and —NHCH (CH$_2$CH$_2$COO$^-$)COO$^-$, R represents either an ethyl or benzyl, m is an integer selected from the group consisting of 2, 7, 12 and 16, and n is an integer selected from the group consisting of 0, 1, and 3, comprising the steps of:.

(a) reacting the poly(alkoxyethyleneglycol)alkali metal salt of Formula 3 with a hexachlorocyclotriphosphazene of Formula 4 in the molar ratio of 3~4:1 in an organic solvent to prepare a stereo-specific cyclotriphosphazene intermediate of Formula 5;

MO—(O)$_{\overline{m}}$(CH$_2$)$_n$CH$_3$ (3)

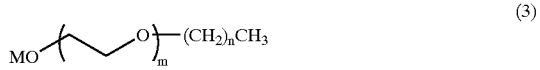
(3)

wherein M is sodium or potassium, and m and n are identical to those defined in Formula 1

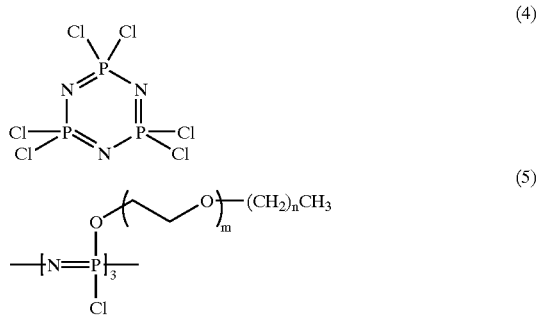
(4)

(5)

wherein m and n are identical to those defined in Formula 1, and (b) reacting the cyclotriphosphazene intermediate of Formula 5 with an amino acid ester of Formula 6 in the molar ratio of 1:3~6

R.ANH.HCl (6)

wherein HNA and R are identical to those defined in Formula 1.

3. A method according to claim 2, wherein poly (alkoxyethyleneglycol) alkali metal salt of Formula 3 is obtained by the reaction of poly(alkoxyethyleneglycol) of Formula 2 and an alkali metal, sodium or potassium:

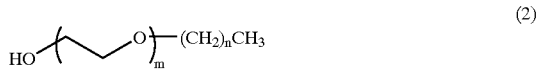
(2)

wherein m and n are identical to those defined in Formula 1.

4. A method according to claim 2, wherein step (a) and step (b) are carried out in the presence of triethylamine.

5. A method according to claim 2, wherein the organic solvent is tetrahydrofuran, toluene or benzene.

6. A method according to claim 2, wherein precipitation is induced by the addition of ethyl ether or hexane after step (b).

7. A method according to claim 6, wherein the precipitates are purified by repeated reprecipitations using a solvent pair of acetone and hexane and then by dissolving in ethyl acetate and extracting with water or by dissolving in water and dialyzing by using a dialysis membrane.

8. A method according to claim 7, wherein the dialysis membrane has a molecular weight cut off of less 1000.

9. A method of claim 7, further comprising purifying a cyclotriphosphazene compound of Formula 1 which contains trace isomers by dissolving in distilled water the purified product obtained by the extraction or dialysis procedure of claim 7 and by adding a LCST lowering agent to the solution to induce precipitation to obtain a product that can be centrifuged.

10. A method according to claim 9, wherein the LCST lowering agent is selected from the group consisting of NaCl, KCl, CF$_3$CH$_2$OH and CH$_3$(CH$_2$)$_3$OH.

* * * * *

UNITED STATES PATENT AND TRADEMARK OFFICE
CERTIFICATE OF CORRECTION

PATENT NO.     : 6,417,383 B1
DATED          : July 9, 2002
INVENTOR(S)    : Youn Soo Sohn et al.

It is certified that error appears in the above-identified patent and that said Letters Patent is hereby corrected as shown below:

<u>Title page,</u>
Item [87], PCT Pub. No.:, change the PCT Publication No. from "WO01/30668" to -- WO01/32668 --.

Signed and Sealed this

Twelfth Day of November, 2002

Attest:

Attesting Officer

JAMES E. ROGAN
Director of the United States Patent and Trademark Office